US00PP15559P3

(12) United States Plant Patent
Zima

(10) Patent No.: US PP15,559 P3
(45) Date of Patent: Feb. 15, 2005

(54) FLOWERING CRAB APPLE TREE NAMED 'UEBO'

(50) Latin Name: *Malus mill.*
Varietal Denomination: Uebo

(75) Inventor: Jan Zima, Turnov (CZ)

(73) Assignee: Institute of Experimental Botany (CZ)

( * ) Notice: Subject to any disclaimer, the term of this patent is extended or adjusted under 35 U.S.C. 154(b) by 0 days.

(21) Appl. No.: 10/409,944

(22) Filed: Apr. 9, 2003

(65) Prior Publication Data

US 2004/0205868 P1 Oct. 14, 2004

(51) Int. Cl.[7] ..... A01H 5/00

(52) U.S. Cl. ..... Plt./173

(58) Field of Search ..... Plt./173

*Primary Examiner*—Kent Bell
*Assistant Examiner*—W C Haas

(74) *Attorney, Agent, or Firm*—Webb Ziesenheim Logsdon Orkin & Hanson, P.C.

(57) ABSTRACT

A new and distinct *Malus mill.* plant having a weeping, dense habit and persistent fruit.

5 Drawing Sheets

Botanical classification: *Malus mill.*
Varietal denomination: 'Uebo'.

BACKGROUND OF THE INVENTION

The present invention comprises a new and distinct cultivar of flowering crab apple tree botanically classified as *Malus mill.* and known by the varietal name 'Uebo'. The new variety was discovered in 1998 as a weeping, dwarf crab apple seedling of unknown parentage in Vlastiborice Village near Turnov, Czech Republic. The following characteristics distinguish the new variety from other *Malus mill.* Varieties known to the inventor.

Dwarf growth
Small tree size
Weeping, dense habit
Thin shoots
Fine branches
Fine narrow leaves
White flowers
Strong annual blooming
Fruit persistent into winter
Small, bright carmine red fruit Table 1 compares the new variety to 'Red Swan' (U.S. Plant Pat. No. 6,974):

TABLE 1

| Similarities | Differences |
|---|---|
| Excellent weeping habit | 'UEBO' has a dwarf growth habit, small-sized tree |
| Fine, narrow leaves colored gold in the fall | 'UEBO' has snow white flowers |
| Small red fruits persist into winter | 'UEBO' has fruit that is shaped globose-conical |

The new variety has been trial and field tested and has been found to retain its distinctive characteristics and remain true to type through successive propagations.

DESCRIPTION OF THE DRAWINGS

The accompanying photographic drawings illustrate the new cultivar, with the color being as nearly true as is possible with color illustrations of this type.

DESCRIPTION OF THE PLANT

Figure 1:
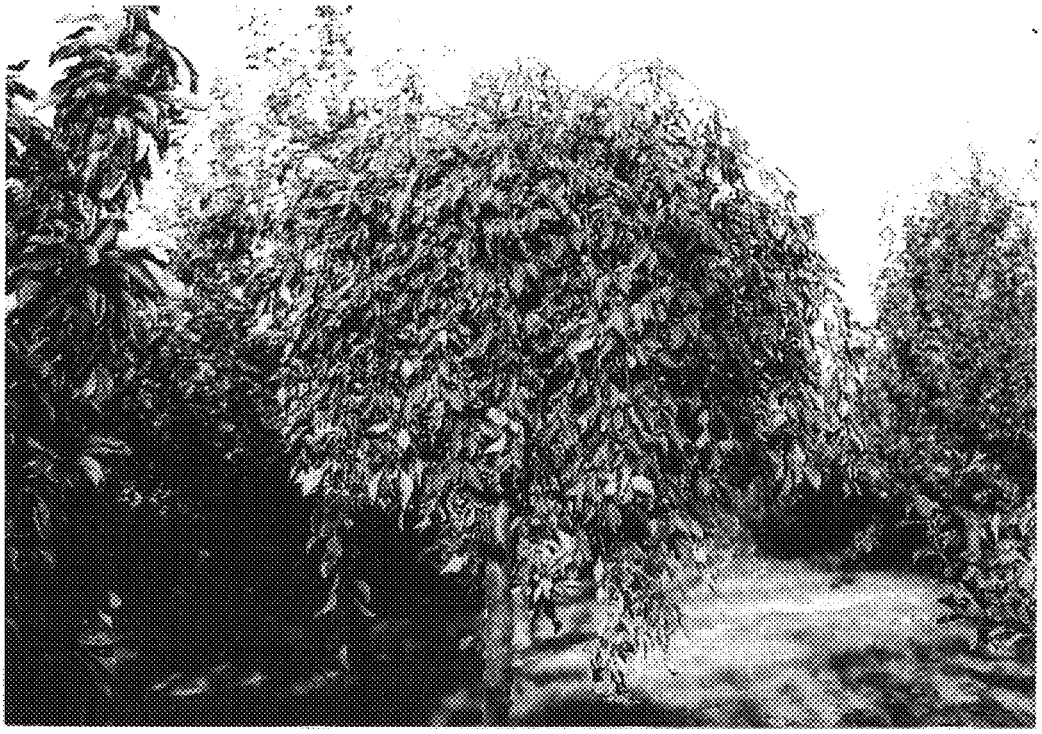
FIG. 1 is a photograph of the new variety bearing fruit.
Figure 2:
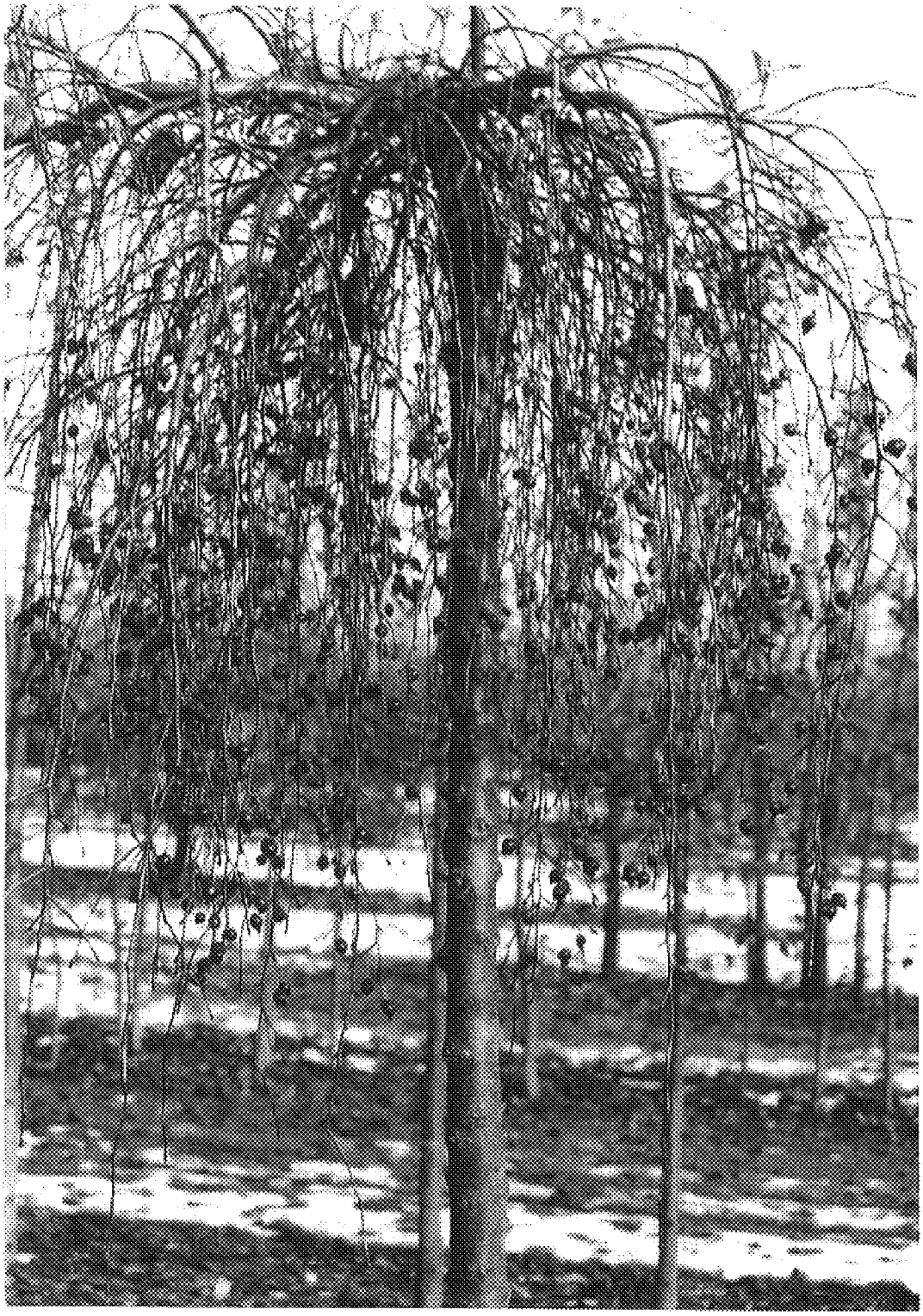
FIG. 2 is a photograph of the new variety in the winter.
Figure 3:
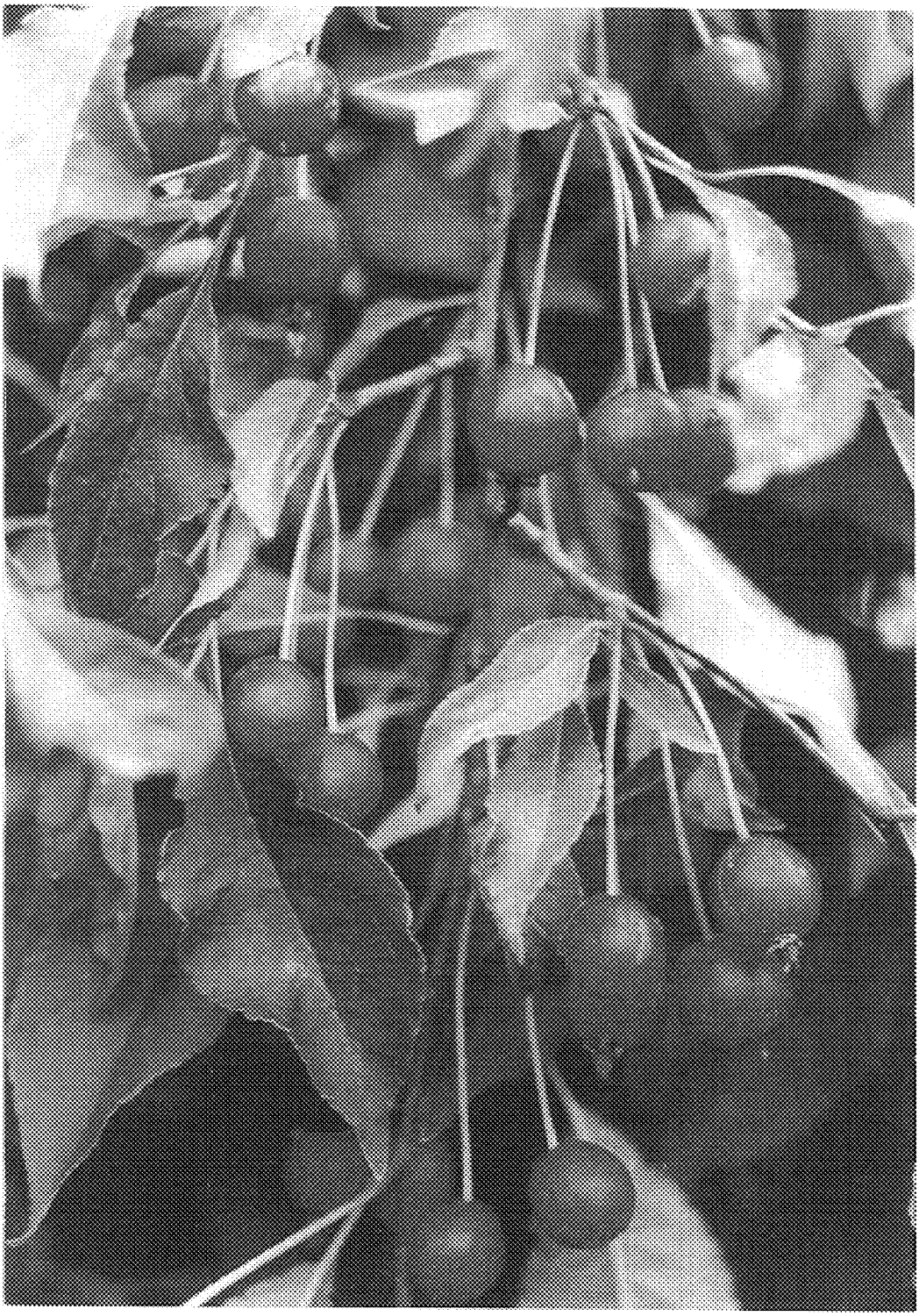
FIG. 3 is a close-up view of the fruit of the new variety.
Figure 4:
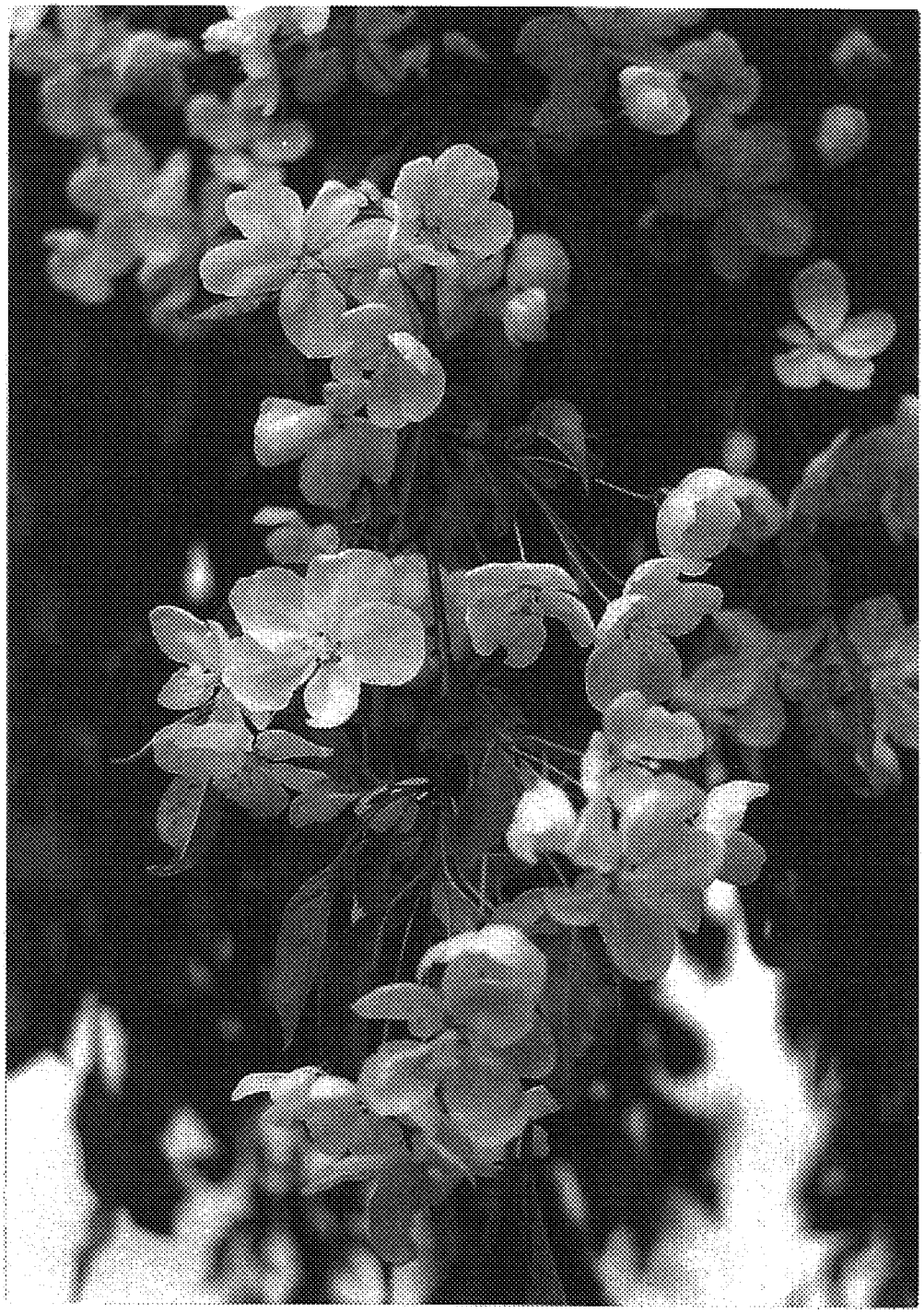
FIG. 4 is a close-up view of the blooms of the new variety.
Figure 5:
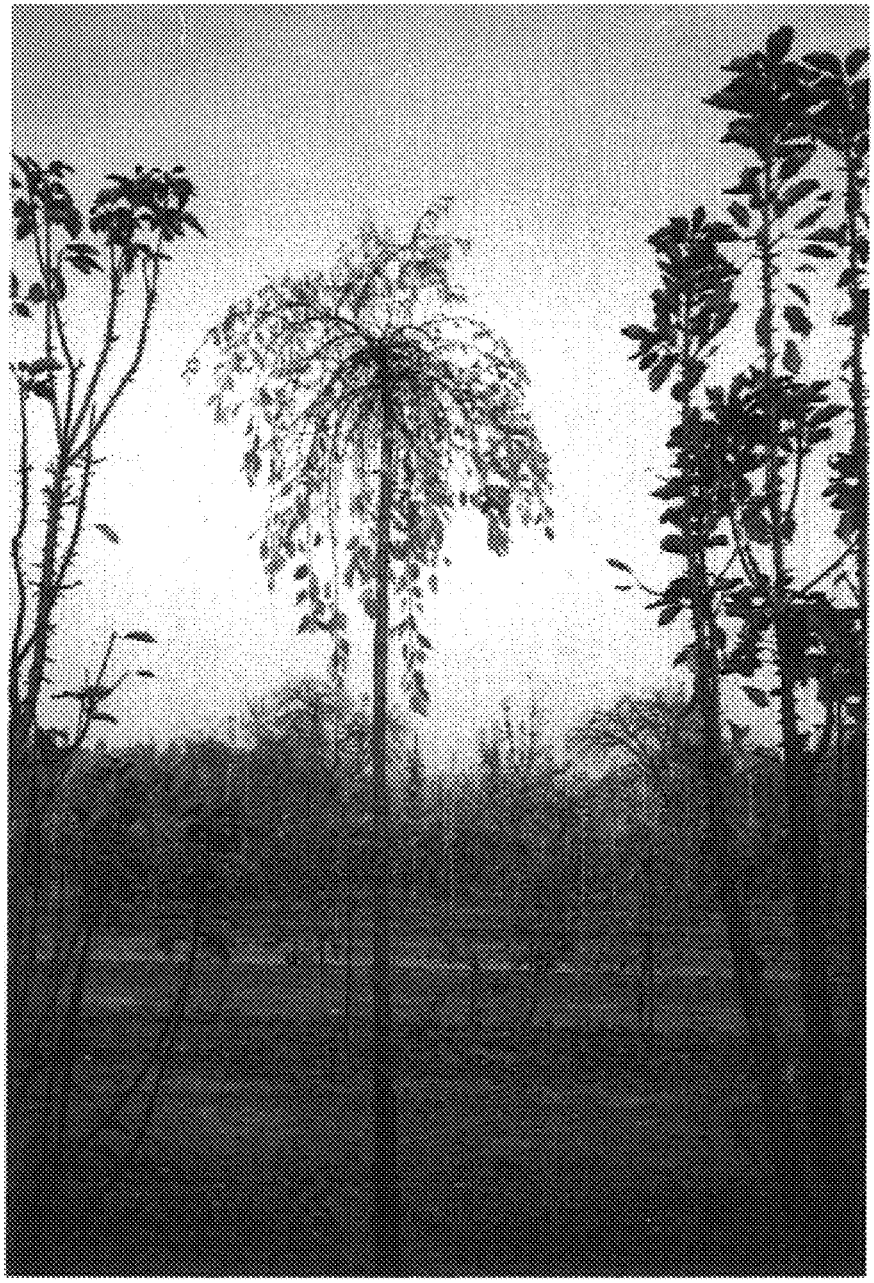
FIG. 5 is a photograph of the new variety without fruit.

The following detailed description sets forth the characteristics of the new cultivar. The data which defines these characteristics were collected by asexual reproductions by grafting and budding on apple rootstocks first carried out near Turnov, Czech Republic in the spring of 1998. Plants were grown in free soil under field conditions having a mean year temperature of 7.7° C. and a mean precipitation amount of 680 mm/year. The following fertilizer combination was used (kg/ha/year): 55 parts nitrogen, 25 parts phosphorous, 60 parts potassium, 55 parts calcium, and 5 parts magnesium. The color readings were taken in natural daylight. Color references are primarily to the R.H.S. Colour Chart of The Royal Horticultural Society of London.

TREE

Age: 5 years after grafting.
Size: The size of the crown of a 5 yr. old tree of the new variety after grafting on a seedling rootstock at a height of 1.8 m is 1 m in both height and spread. A 9 yr. old tree of the new variety grown from seed is 0.7 m in height and 1.6 m in spread.
Vigor: Weak.
Density: Heavy.
Form: Weeping.
Production: High annual bearing.

Growth type: Dwarf; weeping.
Trunk: Exhibits a color of 173A with some 152C.
Branches:
*Diameter.*—At rootstock trunk: 5 cm.
*Surface texture.*—Smooth.
*Color.*—166A.
*Form.*—Fine; dense; weeping.
*Average angle.*—Horizontal arching to vertical.
*Bud arrangement.*—Slightly held out from shoot axis.
*Lenticels.*—Length: 2.5 mm. Width: 0.4 mm. Shape: Mostly elongated; some round. Density: Medium. Color: 199A. Number: 30.
Leaves:
*Shape.*—Lanceolate.
*Length.*—6 cm.
*Width.*—2.5 cm.
*Form.*—Narrow.
*Base.*—Concave.
*Apex.*—Acuminate.
*Margin.*—Serrate.
*Pubescence.*—Absent.
*Color.*—Mature leaves: Upper surface: 146A to 147A. Lower surface: 146A to 147A.
*Petiole.*—Shape: Almost straight. Length: 2.8 cm. Diameter: 1 mm. Color: 144A, with 59A to 59B at the very base.
*Veins.*—Venation type: Standard branched type, medium dense. Color: Upper surface: 144A. Lower surface: 144A.
Flowers:
*Average dates of bloom.*—First: May 10$^{th}$. Full: May 16$^{th}$. Last: May 20$^{th}$.
*Blooming period.*—Long.
*Bud.*—Length: 11 mm. Diameter: 7 mm. Shape: Ovate. Color: 155D to 64C.
*Number of flowers per cluster.*—4 to 5.
*Fragrance.*—Medium to strong.
*Diameter.*—38 mm.
*Depth.*—5.
*Showiness.*—Yes.
*Petals.*—Number: 5. Shape: Broadly elliptic to circular. Color: When opening: Light pink. Fully opened: Upper surface: 155D. Lower surface: 155D.
*Pedicels.*—Length: 4 cm. Diameter: 1 mm. Color: 144B.
Reproductive organs:
*Stamens.*—Number: 15 to 19. Pollen amount: Small. Anthers: Color: 10B to 10C. Shape: Ovate. Length: 1 mm.
*Pistils.*—Number: 1 with 5 styles. Style color: 145A. Stigma: Color: 151B. Shape: Round. Size: Small.
Fruit:
*Maturity when described.*—Fully ripened.
*Size.*—Axial diameter: 1 cm. Transverse diameter: 1 to 1.2 cm.
*Form.*—Globose-conical.
*Average weight of mature fruit.*—0.5 g.
Skin:
*Texture.*—Smooth.
*Tendency to crack.*—No cracking before winter frost.
*Color.*—47A.
Seeds:
*Number perfect.*—2 to 5.
*Number in one cell.*—1.
*Length.*—4 mm.
*Width.*—2.5 mm.
*Shape.*—Ovate.
*Color.*—175A to 175B.
*Fertility.*—80% germinability.
Stem:
*Length.*—5 cm.
*Color.*—Yellow to Yellow-orange.
Use: Small-sized, weeping ornamental crab apple.
Disease resistance: Resistant to scab; tolerant to mildew.
Heat tolerance: No damage observed at the place of origin.
Cold tolerance: Ranges from −20 to 34° C.

I claim:

1. A new and distinct variety of *Malus mill.* plant substantially as shown and described.

* * * * *